US010471013B2

(12) United States Patent
    Jin

(10) Patent No.: US 10,471,013 B2
(45) Date of Patent:     Nov. 12, 2019

(54) PROCESS FOR PRODUCING POLYMERIC MICROSPHERES

(71) Applicant: BIODVERY PHARMATECH, LTD, Pudong District (CN)

(72) Inventor: Tuo Jin, Shanghai (CN)

(73) Assignee: BLODVERY PHARMATECH, LTD, Pudong District (CN)

( * ) Notice: Subject to any disclaimer, the term of this patent is extended or adjusted under 35 U.S.C. 154(b) by 75 days.

(21) Appl. No.: 15/567,840

(22) PCT Filed: Jan. 21, 2016

(86) PCT No.: PCT/CN2016/071572
    § 371 (c)(1),
    (2) Date: Oct. 19, 2017

(87) PCT Pub. No.: WO2016/131363
    PCT Pub. Date: Aug. 25, 2016

(65) Prior Publication Data
    US 2018/0116962 A1    May 3, 2018

Related U.S. Application Data

(60) Provisional application No. 62/185,623, filed on Jun. 28, 2015, provisional application No. 62/118,465, filed on Feb. 20, 2015.

(51) Int. Cl.
    *A61K 9/16*    (2006.01)
    *A61K 38/26*   (2006.01)
    (Continued)

(52) U.S. Cl.
    CPC .......... *A61K 9/1694* (2013.01); *A61K 9/1647* (2013.01); *A61K 38/1816* (2013.01); *A61K 38/26* (2013.01); *A61K 9/0019* (2013.01)

(58) Field of Classification Search
    CPC .. A61K 38/1816; A61K 38/26; A61K 9/0019; A61K 9/1647; A61K 9/1694
    See application file for complete search history.

(56) References Cited

U.S. PATENT DOCUMENTS

2008/0217222 A1*  9/2008  Efraty ............... B01D 46/0013
                                                        210/109
2013/0137782 A1*  5/2013  Shimoda ............. B01F 3/0807
                                                        514/785

FOREIGN PATENT DOCUMENTS

CN    1487258 A     4/2004
EP    0481892 B1    3/1996
          (Continued)

OTHER PUBLICATIONS

"International Application No. PCT/CN2016/071572, International Preliminary Report on Patentability dated Aug. 22, 2017", (Aug. 22, 2017), 6 pgs.
          (Continued)

Primary Examiner — Michael B. Pallay
(74) Attorney, Agent, or Firm — LKGlobal | Lorenz & Kopf, LLP

(57)    ABSTRACT

The present disclosure disclosed a microsphere-producing process involving three integrated unit operations, 1) microspheres formation; 2) microsphere quality control; 3) post formation microsphere treatment. The first unit operation, i.e. unit operation 1) is integrated with four essential functions: forcing the particle forming materials to pass through a porous membrane to form embryonic microspheres; enforcing the embryonic microspheres to detach the porous membrane; solidifying the embryonic microspheres; collecting and outputting the solidified microspheres. The quality control unit operation consists discrimination and ejection of oversized microspheres. The post treatment unit operation is integrated with two essential functions, smoothing the
          (Continued)

Figure 2:
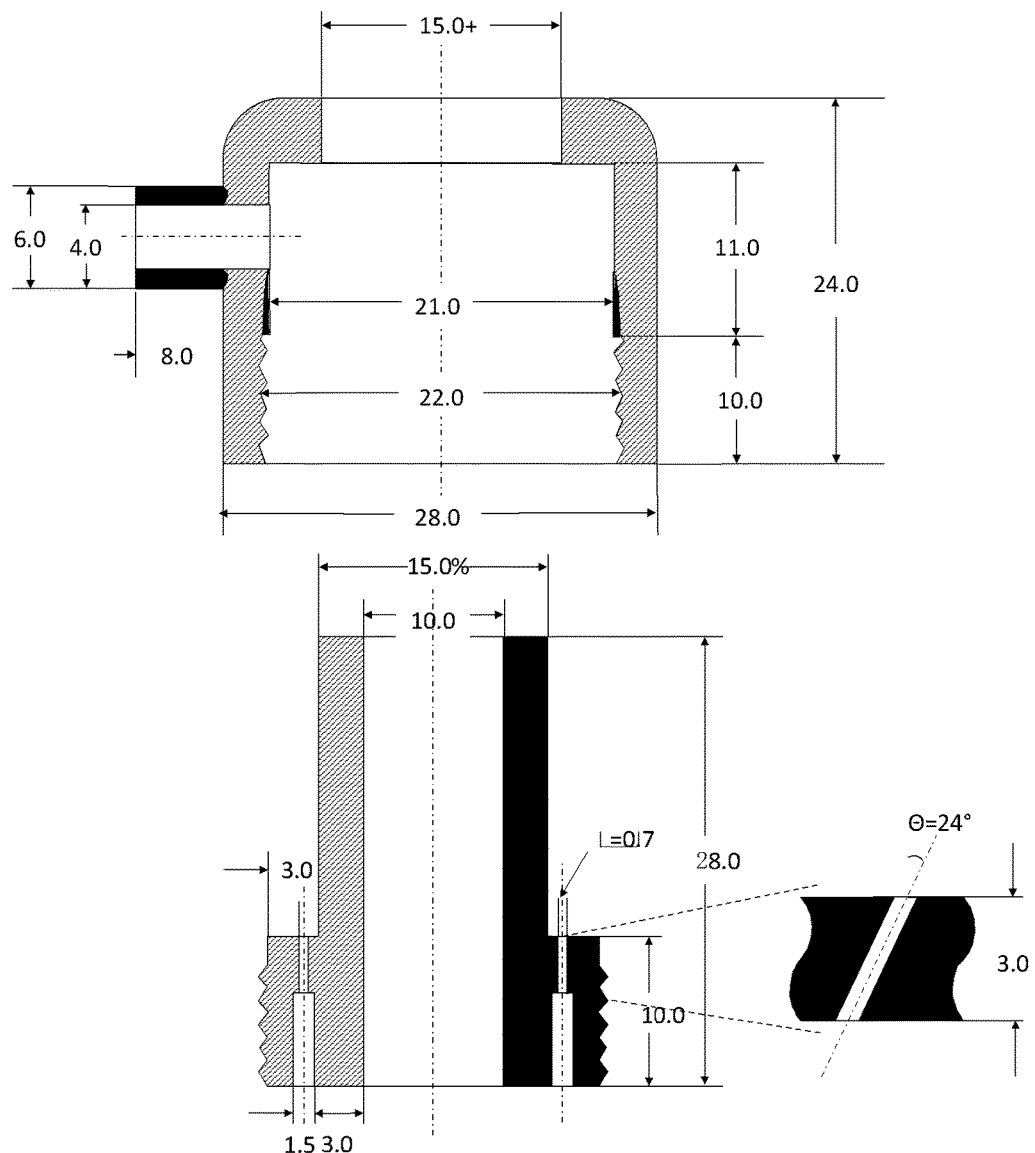

microsphere surfaces and reducing organic solvents trapped inside of microsphere matrix.

21 Claims, 9 Drawing Sheets

(51) Int. Cl.
*A61K 38/18* (2006.01)
*A61K 9/00* (2006.01)

(56) References Cited

FOREIGN PATENT DOCUMENTS

| | | |
|---|---|---|
| WO | 2009053885 A2 | 4/2009 |
| WO | 2014139168 A1 | 9/2014 |

OTHER PUBLICATIONS

"International Application No. PCT/CN2016/071572, International Search Report dated Apr. 19, 2016", (Apr. 19, 2016), 4 pgs.
"International Application No. PCT/CN2016/071572, Written Opinion dated Apr. 19, 2016", (Apr. 19, 2016), 5 pgs.
European Patent Office, Extended European Search Report for Application No. 16751894.3, dated Dec. 3, 2018.

\* cited by examiner

Fig. 1

Size of microsphere: 40-60μm;
Exenatide loading 3.11%;
MW of PLGA: 14K~45K;

PROCESS FOR PRODUCING POLYMERIC MICROSPHERES

CROSS REFERENCES AND RELATED APPLICATIONS

This application claims priority of U.S. Ser. No. 62/118,465 filed on Feb. 20, 2015 and of U.S. Ser. No. 62/185,623 filed on Jun. 28, 2015, the contents of which are incorporated as reference here into this application.

FIELD OF THE INVENTION

This disclosure demonstrates a novel process (method) to prepare polymeric microspheres of designed uniform sizes, improved encapsulation efficiency for soluble ingredients, and reduced number of unit operations. These microspheres may be used to encapsulate bioactive agents (including therapeutic agents) with high loading efficiency and/or preserved native conformation for controlled or sustained release delivery to human and other animals.

BACKGROUND OF THE INVENTION

Polymeric microspheres are successfully used for controlled- or sustained-release delivery of some active agents comprising therapeutics such as chemical drugs or therapeutic peptides. This type of dosage forms has also been used in the attempts to achieve controlled- or sustained-release delivery of proteins. The ability of polymeric microspheres to control or retard release rate of the active or therapeutic ingredients loaded wherein offers a great compliance improvement to patients who have to receive frequent injections of medicine for prolonged period or even life time. With controlled- or sustained-release functions, the in vivo concentration of the medicines (drugs or vaccines) may well be maintained within the therapeutic window (a situation of which in vivo level of a drug/medicine is above the minimum effective concentration but below the minimum toxic concentration). The frequency of the hateful injections may therefore be greatly reduced.

Accompany with the benefits above are some drawbacks. A major challenge for preparing protein-loaded microsphere dosage forms is their sterilization process. Microspheres for sustained-release delivery of biologics are normally 10~100 μm in diameter so that they cannot be sterilized by filtration through a membrane 0.2 μm in pore sizes, a method for sterilizing proteins conventionally. Radiation and heating are out of question too due to the susceptibility of proteins and many other therapeutic agents to such hazardous conditions which result in denaturing and/or degradation of the ingredients. The only feasible method to prepare sterilized microspheres for controlled- or sustained-release delivery of proteins is to prepare this type of dosage forms under an aseptic condition, i.e. to incorporate the whole preparation process in an aseptic environment. Current manufacturing processes produce microspheres of relatively diversified diameters for which pre-lyophilization, sieving and powder-filling become necessary. Sieving and powder-filling are unit operations during which the medical products are exposed to the ambience and difficult to be isolated within an aseptic environment. Moreover, the needs of saving to remove particles of undesired sizes results in reduced yield of manufacture, and powder-filling is difficult to achieve accurate load and requires sophisticated machines. In addition to size dispersion, stirring, a unit operation to prevent microsphere fusion in the present production process, may also result in leaking of the encapsulated. The shear stress generated from stirring may break the newly formed microspheres and expose the encapsulated ingredients to the continuous phase as well as the water-oil (organic phase) interface, a factor known to denature proteins. In addition, under-sized particles are regarded as a source of burst release, and the over-sized microspheres may block the injection needle unless hateful larger needles are selected.

While sustained-release microsphere is the only practical dosage form to date to achieve pro-longed efficacy over two weeks or longer by single injection, this dosage form is used limited drugs due to its production difficulties and other drawbacks. Clearly, a preparation process which enable manufacturer to produce microspheres of uniform and designable particle sizes, and to fill vials with the medicine in a fluid form will be greatly helpful for sterilized manufacturing.

BRIEF DESCRIPTION OF THE INVENTION

The present disclosure demonstrates a method/process to produce microspheres of designable uniform size, 90%+ encapsulation efficiency for water soluble ingredients and smoothen surface for minimal burst release with reduced number of unit operation and operational easiness. This invented process consists three unit operations as formation and solidification of uniform microspheres, identification and ejection of oversized particles, as well as post treatment to smooth the surface of formed microspheres. Each of the unit operations can easily be accomplished by self-consistent process design and/or simplified control factors.

The first unit operation, formation and solidification of microspheres, combines three essential preparation steps in one as, 1) forcing the particle forming materials to pass through a porous wall and detach into a receiving/carrier medium as embryonic (soft) microspheres; 2) solidifying the detached embryonic microspheres by extracting the solvent that dissolves the microsphere-forming materials; and 3) collecting the solidified microspheres for output with minimal amount of the carrier medium. The porous wall of designed pore sizes may also be termed as a porous barrier or a porous membrane having desired pore sizes and in cylindrical shape or other shapes. A cylindrical porous membrane named as "SPG membrane" made by a company called "SPG technology" is a good example. The microsphere forming materials are normally dissolved in a solvent so that they can be squeezed through the pores of the membrane to form embryonic microspheres. The embryonic microspheres out of the surface of the porous membrane must be detached into a receiving/carrier medium in time to avoid touching and fusing with each other at the membrane surface. Therefore, a shear stress or vibration is needed to facilitate detaching of the embryonic microspheres into the carrier medium.

The soft embryonic microspheres detached into the receiving medium must be solidified prior to accessory unit operations; and the solidification process must avoid collision, breaking or fusion of the embryonic microspheres. To achieve this purpose, the receiving or carrier medium must be immiscible with the microsphere-forming materials or its solution, yet be able to extract the solvent or solvents in which the microsphere-forming materials are dissolved. Methylene dichloride and water are good example of such a pair of the solvent to dissolve microsphere forming materials and the receiving medium. The former dissolves many biodegradable polymers, and the later is immiscible with the former but dissolves it in some extent. To avoid touching and fusing with each other, the soft embryonic microspheres should best be driven into a parallel movement towards a collector during the solvent extraction or evaporation (i.e. solidification) process. Two ways are feasible to achieve this purpose, by a flow of the receiving medium to carry the embryonic microspheres away or by the gravity force to drive the embryonic microspheres down to a collector through a solvent extraction path. The later seems simpler than former.

For efficiency of the post treatments, the hardened microspheres should be transferred to the post treatment container with minimal volume of the receiving medium. Therefore, the hardened microspheres are best to be concentrated prior to transfer in order to minimize the receiving phase. The concentrated microspheres must, however, not be packed tightly but retain sufficient amount of the carrier (receiving) medium in order to remain their fluidity for flow-transfer to the accessary unit operations. A microsphere collector that may accumulate the microspheres in such manner and allow them to be driven away with a flow of the carrier medium should be applied. The flow rate of carrier medium should be low enough to limit the medium amount but its velocity should be high enough to give the microspheres sufficient kinetic energy to move up to the post treatment container.

Operationally, the above three processes, microsphere forming and detaching, microsphere solidification (hardening), and microsphere collection and transferring, may achieved by a single unit operation. The simplified operation offers even better quality of microspheres in terms of uniform size, 90%+ encapsulation efficiency, and improved protein stability due to avoiding their contact with water-oil interfaces.

What between the unit operations of microsphere-forming and post-treatment is a quality control unit that is responsible to discriminate and eject oversized microspheres in case that have formed accidently. While few under- or oversized particles formed during the microsphere-forming step do not affect sustained-release profiles of the encapsulated ingredients, one or few oversized microspheres may block the injection needles, for which hateful larger needles may become necessary. To block oversized microspheres to pass through the production line, a screen of selected mesh size is mounted in the tubular pass between the two unit operations. To avoid block the flow, a three-way valve is placed before the mesh screen for ejecting the intercepted oversize microspheres out of the production line. This three-way valve offers three switching positions, to allow the microsphere carrying medium to flow to the post treatment container (through the mesh screen), to eject the intercepted oversize microspheres, and to drain the content in the microsphere-forming and solidifying compartment.

Rinsing is another niche of this simplified process of microsphere production. This operation is designed to accomplish multiple tasks as removing surfactants and salts, smoothing the microsphere surfaces to reduce burst effect, and reducing organic solvent residues trapped in the matrix of the microsphere. To achieve this goal, the solidified microspheres are transferred to a container filled with water for rinsing or with a solvent that may partially swell the surface of the polymeric microspheres. Partial swelling may substantially reduce the phase transition temperature of the polymer form which the matrix of the microspheres are formed, so that the surface of microspheres may be smoothed by mild heating, say below 40° C. The mild heating should not denature biologic ingredients loaded in the microspheres, but should be effective to accelerate the diffusion of organic solvent residues from the center to the surface of the microsphere matrix.

To realize the preparation processes above, a rinsing container endowed with solvent/water input and output, gentle stirring, as well as heating should be equipped. To avoid localized overheating, a heating unit should be attached to the outer surface of the rinsing container, for example a heating jacket well used in chemistry laboratories. The output of the rinsing liquid should also be gentle enough to avoid causing turbulence and exposure of the microspheres to air. The output should also avoid draining the microspheres. Therefore, the water/solvent drainage is carried out from the top of the rinsing liquid. For example, a floating suction port is designed for draining the rinsing liquid from the top of the sample. A mesh should be mounted over the inlet of the floating suction port to prevent microspheres to be sucked in. Even though, the floating suction port possesses an inlet of sufficient large area to minimize the velocity of the draining liquid so that sedimentation of the microspheres will be affected. The floating suction port be guided in a position to avoid collision with the stirrer and the wall of the container. The stirring should be gentle too.

As an important step of quality control, oversized microspheres should be identified and rejected within the production line to ensure that a relatively small needle can be used without the concern of blocking. A convenient opportunity to do so is the moment when the solidified microspheres are being transferred to rinsing and post-formation treatment. Therefore, a screen mesh and three-way valve may be mounted between the microsphere collector under the solidification column and the container for rinsing/post-treatment.

As summary, the invented process allows polymeric microspheres of uniform and designed sizes to be prepared within two practical unit operations, microsphere forming-solidifying-collecting and smoothing-desolvent-rinsing. The simplified production process is environmentally friendly, safe, and offers greatly improved product quality.

To achieve the invented process of microsphere preparation, an apparatus or device comprising a porous membrane of designed pore sizes (such as the cylindrical SPG membrane), a shear stress generator or a vibration generator to detach the formed embryonic microspheres from the membrane, a column or tube to guide the sedimentation or flow of embryonic microspheres through the solvent extraction path to a collector, and a collector at the bottom of which the hardened microspheres are accumulated the prior to rinsing is essential (refers to FIG. 1). The apparatus or equipment should also include a path to out-put the hardened/solidified microspheres to a rinsing/washing container. The path may be set to the bottom of the collector to drain the microspheres out or set inside of the collector to sock the microspheres out by the intrinsic pressure of the receiving phase. In the later case, the path or tube should have a bell-shaped or cone-shaped entrance to guide the microspheres in.

DETAILED DESCRIPTION OF FIGURES

The figures are served to help readers to understand this disclosure, so that they should not be used to limit this disclosure.

FIG. 1. The apparatus the microsphere-forming and solidifying unit comprising a porous membrane of designed pore sizes (such as the cylindrical SPG membrane), a shear stress generator or a vibration generator to detach the formed microspheres from the membrane, a column or tube to guide the sedimentation or flow of embryonic microspheres through the solvent extraction path to a collector, a collector to accumulate hardened/solidified microspheres, and a tube with a draining valve or a bell-shape entrance to output the microspheres. The solvent extraction path can be set as vertical or other orientation. The socket tube for outputting microspheres may be set at the bottom of the collector or at inside of the collector. The microsphere collector has a rounded, cylindrical or cone shape bottom. The shear stress generator or the vibration generator should create a relative motion by flowing, turning, shaking, or vibration between the membrane and the carrier medium. The connection between the solvent extraction path and the microsphere collector can be different form and sizes if it allows microspheres to pass through. The diameter of solvent extraction path and the volume of microsphere collector may be enlarged to meet the needs of pilot production and massive manufacture.

FIG. 2. A design of a ring-shape nozzle for stirring the water and creating a shear stress along the porous membrane surface of FIG. 1. The nozzle can be mounted on the tube connected with the porous membrane is mounted. A nozzle of straight-tube shape may also be used depends for externally pressed porous membrane.

Figure 3:
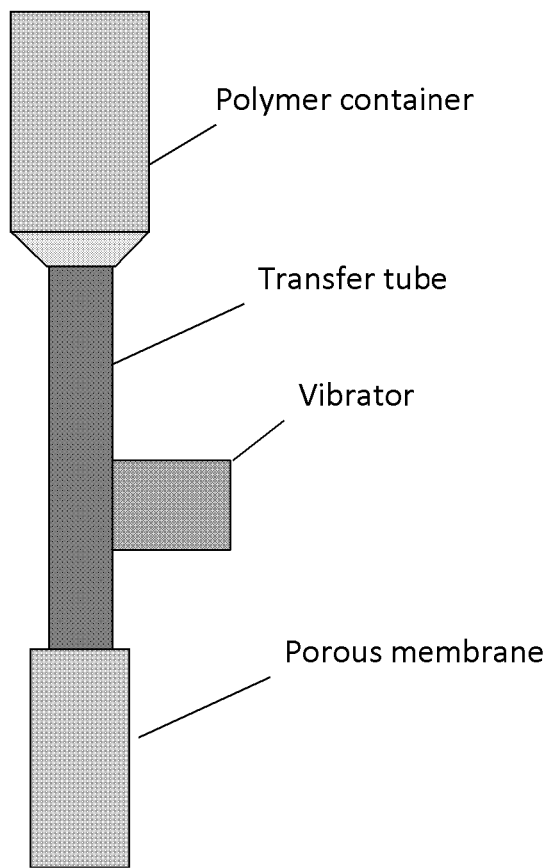

FIG. 3. A design of a vibrator-attached microsphere-forming unit, comprising a container of microsphere forming materials, a connection tube to lead to SPG membrane, and the SPG membrane for squeezing the embryonic microspheres out. That is, the vibrator attached on the container or the connection tube to shack the embryonic microspheres (the formed droplets) away from the membrane surface of FIG. 1.

Figure 4:
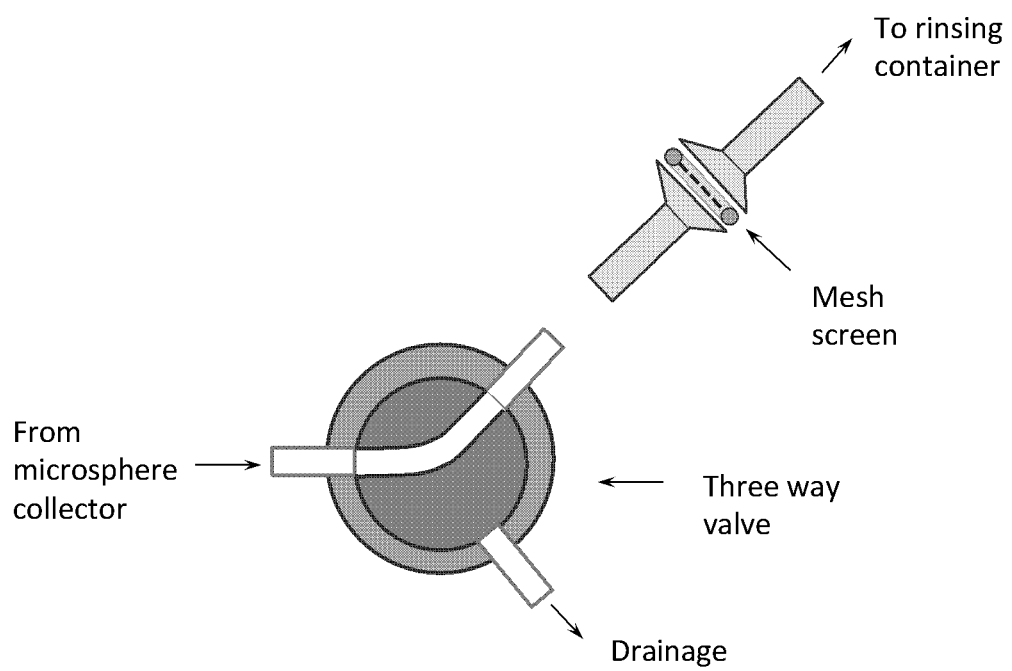

FIG. 4. A design of a quality control unit that discriminates and ejects oversized microspheres, comprising a mesh screen and a three-way valve.

Figure 5:
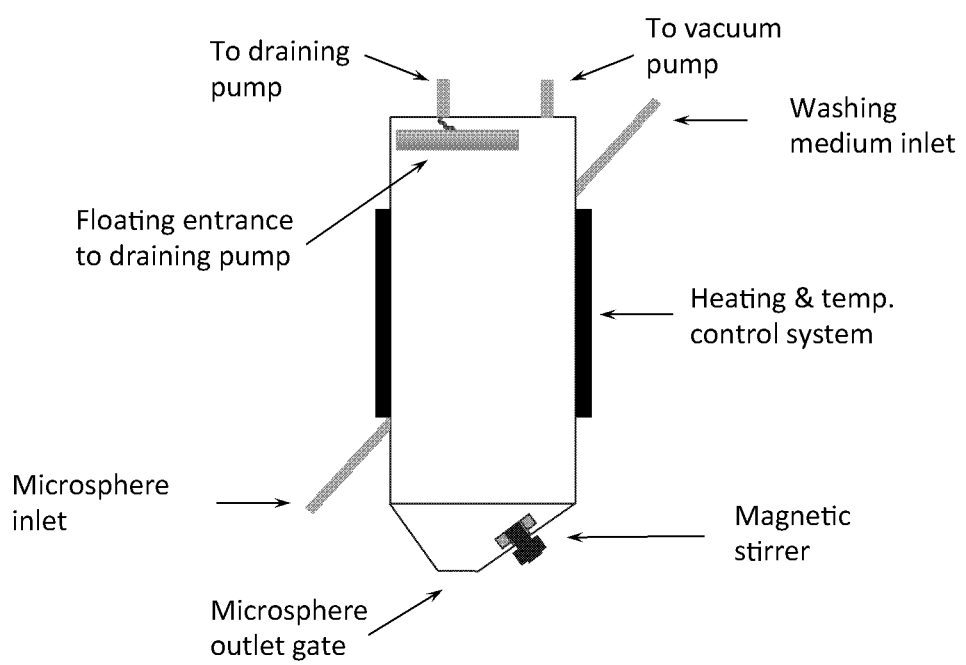

FIG. 5. A design of a post-treatment unit for smoothening and rinsing the hardened microspheres, comprising a microsphere-rinsing container, a stirrer, a flouting supernatant draining part, heating system to control the treatment temperature, and gate valve to discharge treated microspheres.

Figure 6:
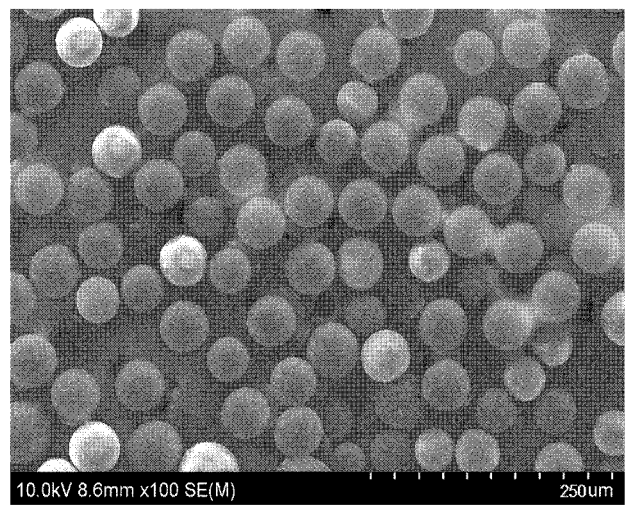

FIG. 6. Electron microscopic image of exenatide-loaded microspheres which were prepared by the process of this disclosure using the apparatus described in FIG. 1. The particle diameter is as uniform as within 40~60 μm.

Figure 7:
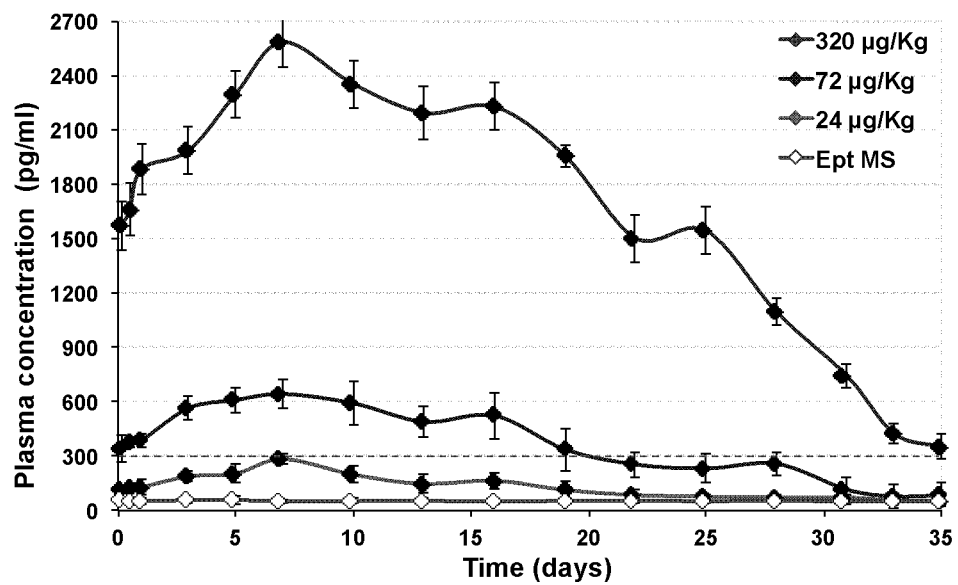

FIG. 7. Blood concentration curve of exenatide in monkeys resulted from injecting monthly-acting microsphere formulation prepared by the process of this disclosure and apparatus in FIG. 1. Since the release kinetics was near to perfect, the dose (converted from monkey to human) to reach the targeted blood concentration (300 pg/ml) was only 25% of the commercial weekly-acting exenatide microsphere dosage form, Bydureon.

Figure 8:
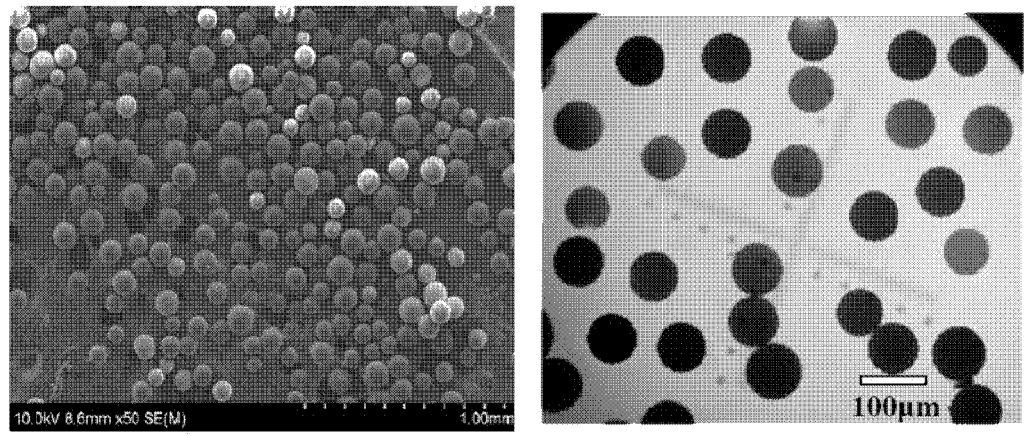

FIG. 8. Electron and optical microscopic images of erythropoietin (EPO)-loaded microspheres which were prepared by the process of this disclosure using the apparatus described in FIG. 1. Both of images confirmed formation of microspheres of uniform diameter.

Figure 9:
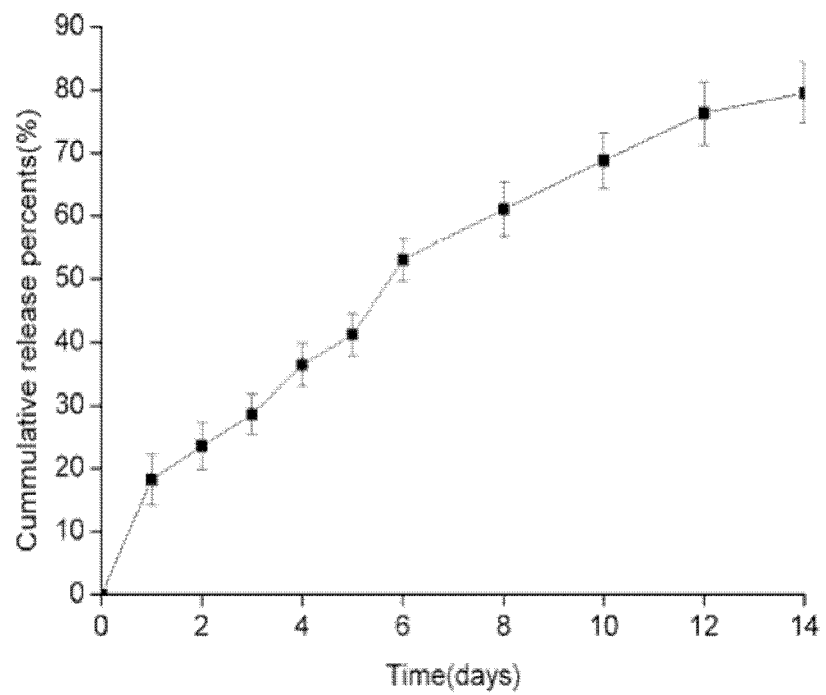

FIG. 9. Cumulative release curve of EPO from the microspheres which were prepared by the process of this disclosure and apparatus in FIG. 1.

Figure 10:
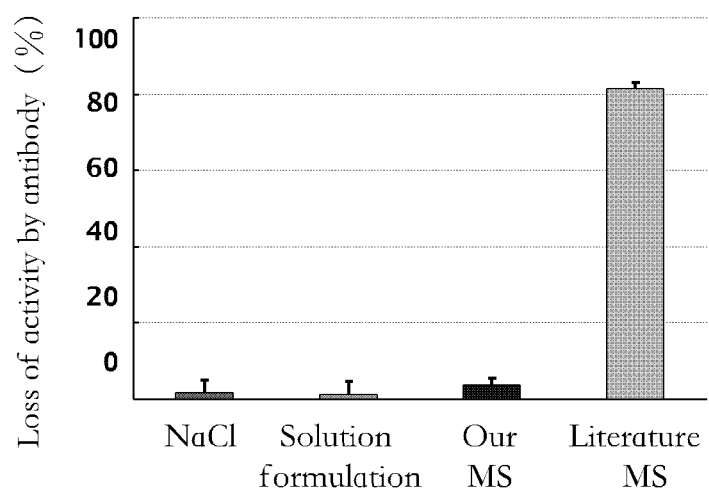

FIG. 10. Activity los of EPO by antibody generation in monkeys after various formulations were injected.

DETAILED DESCRIPTION OF THE INVENTION

The challenges in manufacturing microspheres, especially those used for therapeutic injections, include difficulty to sterilize, diversifying in particle diameter, low encapsulation efficiency, and initial burst release. Each of challenges is self-existing, yet functioning as the source of other problems. They cannot be solved one by one independently. As a practically feasible approach, the multiple issues must be resolved simultaneously and handily. The present disclosure teaches a greatly simplified process and related apparatus design to prepare microspheres of uniform diameters, efficient encapsulation of target ingredient, improved release kinetics and preserved protein conformation Overall Design of the Process This easy-operating production process of microspheres consists two unit operations, microsphere forming-solidification-collection and microsphere smoothing-desolventizing-rinsing. Physically, the process consists three compartments from the top to the bottom (if vertically mounted), sample loading compartment, sample heating-rinsing compartment and sample refrigerating compartment.

Control of Microsphere Sizes

The microspheres of uniform size are formed by squeezing the forming material(s), normally a polymer solution carrying drug agents through porous wall (barrier or membrane, the three terms may be used alternately below) of designed pore sizes into a received phase, normally water-based solution. The formed embryonic microspheres (the drug-carrying polymer solution drops) must be driven away from the surface of the membrane sufficiently fast by shear stress or vibration to avoid fusion with each other before detaching. In order to detach the formed embryonic microspheres away from the surface of the porous membrane in time, a flow generator to create a gentle water flow to blow the droplets away or a vibrator to shack the container where the droplets come out. FIGS. 1, 2 and 3 describe how the flow creator and the vibrator is designed and attached on the system. The designs in the Figures are for those skilled in the art to understand the said engineering principle easily. They should not be used to limit the present invent within the particular design because any forms of flow generator or vibrator may serve this purpose.

The flow generator may be a stirrer circulating around the porous membrane or a nozzle to blow a water flow. The rate of the stirrer circulation is between 50 and 500 r/min, and the flow rate form the nozzle should be adjusted between 100~5000 mL/min (with the best flow rate between 200~1000 mL/min). The vibrator is attached to a tube on which the porous membrane is mounted, and the frequency of the vibrator should be adjusted within 100~500/min, with the best to be 200~400/min. Vibrating, shacking or beating the membrane or its holder may also be achieved by placing an internal stirrer magnetically or mechanically.

The drug agents may be chemicals or biologics. The biologics comprise proteins, peptides and nucleic acids such as siRNA or genes. The biologics may be loaded in the microsphere-forming polymer solution in the form of dispersed solution droplets or solid particles.

Solidification of Embryonic Microspheres

The microspheres newly formed from the porous membrane, named embryonic microspheres hereafter, must be received by a continuous phase in which the embryonic microspheres can be suspended and solidified. The continuous phase must be immiscible with the particle (microsphere)-forming materials so that the embryonic microspheres may be kept in shape. On the basis of the immiscibility, the continuous phase should be able to dissolve, in some extent, the solvent or solvents in which the microsphere-forming material or materials were dissolved.

By extracting the solvent from the embryonic microspheres, the microspheres formed through the porous membrane may be solidified.

In order to maintain the designed uniform size, the soft embryonic microspheres must not collide and fuse with each other or break by shear stress associated with stirring during the solidification process. The unit operation currently used in microsphere solidification comprises stirring of the receiving continuous phase to limit fusion between the embryonic microspheres. Since the dynamic motion of the embryonic microspheres increases the chance of collision between the droplets on the contrary, stirring does not prevent fusion but break the fused larger microspheres due to their relatively less shear strain. In another word, stirring controls the particle size by the equilibrium between breaking and fusing of the embryonic microspheres.

In the present disclosure, anti-collision of embryonic microspheres is achieved by "parallel motion" of the newly formed droplets through a long path, during which the solvent of the polymer is gradually extracted into the receiving phase. The solvent-extracting path can be mounted vertically or in other orientations, through which the embryonic microspheres are settling under gravity force or flow by other driving forces. The vertical path through which the embryonic microspheres achieve parallel motion by sedimentation is one of the simplest way of set up.

The stirring-free microsphere solidification may offer another advantage that the leaking of the soluble ingredient encapsulated in the microspheres may be avoided or reduced. Since the process is free of shear stress, the embryonic microspheres will not break, so that the chance for encapsulated soluble ingredients to be exposed to the continuous phase is greatly reduced. Moreover, if the encapsulated ingredients are delicate proteins, preventing exposure to the aqueous continuous/receiving phase means preventing the contact of the macromolecules with water-oil (the water-immiscible polymer solution) interface, a factor known to denature proteins. Surfactants, salts and other excipients required for facilitating microsphere formation may be added in the receiving phase as same as in a stirring container.

Temperature of Receiving Phase

To shorten the distance of microsphere sedimentation or a path of other orientation, temperature of the receiving continuous phase may be adjusted to increase the solubility of the solvent or solvents with which the microsphere-forming materials are dissolved. For example, the water solubility of a commonly used solvent for preparing polymeric microspheres, dichloromethane, increases from 2% to 5% when water temperature drops from 25° C. to 2° C. Increased solvent solubility will facilitate solvent extraction.

Microsphere Collecting and Outputting

The microspheres hardened by solvent extraction through the long path and settled in the bottom of the container, if it is vertical, should best be concentrated and output with minimal volume of the continuous/receiving phase. Minimizing the volume of the continuous phase is essential for improving the efficiency of rinsing the microspheres to remove the residues of the organic solvent in the matrix of microspheres and the excipients in the continuous phase. Design of the container for the continuous phase should facilitate the microsphere concentration. FIG. 1 shows, but not limits to, a design of the bottom of the container by which hardened microspheres may be accumulated and concentrated. The center of the container for collecting microspheres may be deepened to allow microspheres to slide in and accumulated. The deepened part may be cylindrical, rounded, or cone shape. The end of the bottom of the container should also be flat when pipe socket method is used in order to minimize the dead volume for transferring the solidified microspheres.

Transferring Microspheres to Post-Solidification Treatment

Output of the accumulated microspheres may be achieved via various methods. FIG. 1 shows, but not limits to, two output designs, draining the accumulated microspheres from the bottom, or socking them up through a pipe socket. The pipe socket has a bell-shaped or cone-shaped entrance. Another alternative may be that the hardened microspheres are output along the tangent of a flat bottom of the container of the continuous phase by pumping (not shown in FIG. 1). One key setup mechanism is that the gap between the bell- or cone-shape entrance and the bottom of the container should be small enough to create a sufficient velocity of the receiving liquid at a reasonable flow, by which the microspheres can be carried away. The gap should be optimized between 1 and 20 mm, with the most appropriate range between 3 and 10 mm, depends on production volume.

In-Line Quality Control

While the present disclosure of microsphere production process is bale to produces microspheres of designable uniform sizes, quality control to ensure elimination of over-sized microspheres is still critical. One of the drawbacks of sustained-release microsphere formulation is the unavoidable usage of thicker needles. It is always appreciated if the injection needles can be as small as possible. However, if few or even one oversized microsphere(s) is included in the shot, the needle may be blocked. For efficient production, an inline quality control setup to eliminate oversized microspheres will be the ideal design. In this disclosure, such a quality control unit is placed between the two unit operations, 1) microsphere forming, solidifying, and collecting, and 2) microsphere smoothing, solvent removal, and rinsing. This quality control unit possesses two functions, block oversized microspheres selectively and eject oversized microspheres out of the production line. For the former, a mesh screen is mounted in the tube connecting the microsphere collector to the microsphere post treatment container; while for the later, a three-way valve mounted behind the mesh screen. The three-way valve connects three units, A) the microsphere collector, B) the post-encapsulation treatment container and C) a disposal container. By opening the path from A to B, microsphere production is proceeding; by opening the path from A to C, the contents in the microsphere solidification column and the collector can be drained out; by opening the path from B to C, the oversized microspheres intercepted by the mesh screen can be discharged. The quality control unit is schematically described in FIG. 4. For efficient drainage and discharge, the position of the three-way valve should be as lower as possible, but above of the refrigeration compartment.

Preparation Scale

The preparation scale of the microencapsulation process above may easily be adjusted by varying the volume of the receiving (continuous) phase, e.g. the size of the porous membrane mentioned above, the diameter of the tube for the sedimentation path, and the microsphere collection container. The preparation scale can therefore vary from few hundreds of milligrams to nearly a kilogram.

Continuous Production

For continuous production, the microsphere-receiving phase may be added in and drained (or socked from inside) out simultaneously and continuously. Two synchrotron valves to control the adding and draining (or socking) will be helpful. It is recommended that the adding and draining 9socking) the receiving phase slowly so that sedimentation or flow of the microspheres will not be affected.

Preparation of Microspheres Carrying Solid Particulate Ingredients

Some therapeutic agents, proteins for example, need to be protected prior to be encapsulated in polymeric microspheres most of them are made of hydrophobic materials. In this case, a common strategy is to pre-formulate the delicate agents into fine particles, so that the agents may be encapsulated into microspheres in solid form. This microencapsulation process is called "solid-in-oil-in-water" (S/O/W) process. The present disclosure may also be applied to S/O/W method. The modification of the present microencapsulation process to meet the requirements for S/O/W method is to suspend the pre-formulated fine particles in the solution of the polymeric materials of which the matrix of microspheres are formed.

Since solid particles may settle to the bottom of the container of the polymer solution, continuous stirring or shacking may be needed. One of the convenient methods is to apply a magnetic field around the polymer solution container to drive a magnetic stirring bar inside the polymer solution. In the examples of present disclosure, the magnetic field was created by mounting a coil of electric wire around the container and applying electric power to the coil. Pressured air (or other gas such as nitrogen) is then introduced into the container to press the polymer solution, wherein protein-loaded fine particles are suspended, to pass through the porous membrane. The operations for hardening and collecting of the embryonic microspheres containing the protein-loaded particles will be the same as above.

Annealing of Hardened Microspheres

To reduce initial burst of the release of encapsulated ingredients from the hardened microspheres, the surface of the microspheres may better be smoothed by an annealing treatment to eliminate pores formed in the solvent extraction step. The annealing treatment may be incorporated in the preparation process disclosed in the present disclosure.

For polymeric microspheres, annealing treatment is a process to induce phase transition or partial phase transition of the polymeric materials from hard glassy state to a soft gel state. Microspheres will be heated up to reach or over their phase transition temperature to soften the polymer to heal the pores on the microsphere surfaces. The temperature for annealing treatment is, however, affected by the medium used to suspend the microspheres. For example, if polylactic-co-glycolic acid (PLGA) is used to prepare microspheres, the annealing temperature may be lowered by suspending he microspheres in an aqueous solution containing polyethylene glycol (PEG). The concentration and molecular weight of PEG may be adjusted to achieve a designed annealing temperature. In the case of nearly 100% PEG-400, for example, the microsphere surfaces may be smoothen at room temperature. Reducing the concentration of PEG-400 to 80% may result in drastic increase in the phase-transition temperature of PLGA, say 35° C. for example. In addition to PEG, other reagents soluble in water but possessing some lipophilicity may also be used for lowering the temperature in the annealing treatment of PLGA microspheres.

Rinsing of the Microspheres

The formed microspheres need to be well washed to remove unnecessary and undesired components applied or involved in the production process before filling into vials or pre-filled injectors. The process of washing/rinsing the microspheres includes repeated operation of gentle stirring the particles in fresh water or aqueous solution, aging treatment of the microspheres in the washing liquid, as well as removing the washed supernatant. The efficient design for the rinsing process is that it can be accomplished with the post-microencapsulation treatment (also called aging treatment) at the same time. Since aging of the microspheres takes time, fast rinsing involving enforced filtration of microspheres from the washed supernatant becomes unnecessary. The microspheres can therefore be separated from the supernatant by gentle sedimentation to prevent damaging the microspheres, if vertical solidification path is used. To avoid re-stirring the settled microspheres, drainage of the supernatant should best be accomplished by pumping from the top of the washing water. For this purpose, a floating inlet is used for the top water pumping. The entrance of the pumping inlet should be large enough to lower the velocity of the draining, and should be covered by a mesh screen to prevent microspheres from being pumped.

Filling the Final Products

Another important advantage of the present disclosure is that filling of the vials with the microsphere drug product may be achieved by fluid filling. In the case of current manufacture processes, because particle sizes of the microspheres are diversified, a formulation has to be dried into powder and sieved to remove over- and lower-sized particles. Larger microspheres may plug the injection needles while smaller particles may result in burst release. Since the preparation process of the present disclosure enables manufacturing uni-sized microspheres, sieving and powder filling, the unit operations difficult to incorporate into an aseptic production line, may be avoided. The collected microspheres may be annealed (if necessary), rinsed, and mixed with a solution of viscosity-adjusting agent (carboxyl methyl cellulose for example), and then filled into product vials by fluid filling, an unit operation easier to achieve. Fluid filling may greatly simplify mixing and filling as compared with a powder filling process.

The Apparatus

An apparatus that enable the invented microencapsulation process to be accomplished with great easiness and product quality comprises three basic components, the microsphere formation and solidification unit, the particle size control unit, and the post treatment unit a porous barrier to allow microsphere-forming solution to pass through to form embryonic microspheres, a path of receiving medium through which the embryonic microspheres are hardened via solvent extraction, and collector to collect hardened microspheres. The collector is connected with a draining tube at the bottom or mounted with a socket tube inside of the collector. The tube mounted inside having a bell shape or cone shape entrance. The system should also be equipped with a final formulation container to mix all the additives in the final formulation prior to filling into drug vials or trays.

EXAMPLES

The examples below are part of our on-going research of similar formulations and for helping readers to comprehend the disclosure better. The examples should not be used to limit applications of the present disclosure.

Example 1. Microsphere Formulation of Exenatide

Microsphere-forming polymer, PLGA/PLA, was dissolved in methylene dichloride; and exenatide was dissolved in DMSO. Then the two solutions were mixed and added in a container connected to a cylindrical porous membrane. Pressed air or nitrogen (or other gas) was applied in the container to squeeze the mixed solution through the porous membrane into a receiving phase containing polyvinyl alcohol (PVA) and NaCl. The receiving phase was contained in a column 1600~1800 tall and connected with a microspheres collecting bottle. The embryonic microspheres squeezed through the porous membrane were settled from the top to the bottom of column and the bottle under gravity force for approximately 30~40 second, during which the microspheres were hardened. The hardened microspheres were outputted through an inside socket tube with a bell-shape entrance under the water pressure within the tall column to another container for rinsing. The water rinsed microspheres were imaged using an electron microscope to confirm their uniform size (FIG. 2), and then lyophilized for future use. The diameter of the particles is around 40~50 μm.

In some cases, fine powders of $Mg(OH)_2$ or $MgCO_3$ were added to the polymer solution loaded with exenatide prior to subjecting to the porous membrane. To improve release kinetics, the hardened microspheres were annealed at elevated temperature up to the polymer's phase transition point (Tg). In case the drug stability was in concern, Tg of the polymer was adjusted (lowered) by adding PEG into the annealing medium.

To examine the release kinetics, the microspheres were injected to normal monkeys subcutaneously, followed by blood taking and blood exenatide measurement at programed time. As shown in FIG. 4, a month-long constant blood concentration was resulted by single injection of the microsphere formulation.

Example 2. Microsphere Formulation of EPO

Pre-formulated polysaccharide fine particles in which EPO was loaded through an aqueous-aqueous emulsion or freezing-induced phase separation were mixed with the PLGA/PLA solution same as that in Example 1. The formed suspension was then loaded in the container connected to porous membrane (SPG membrane) and squeezed with pressed nitrogen through the membrane into a receiving phase same as that in Example 1. All the successive steps are the same as those in Example 1. The morphology of the microspheres were imaged using an electron microscope and an optical microscope to confirm their uniform sizes (See FIG. 5). The particle diameters were around 70~80 μm.

To examine PEO release kinetics and the protection effect of the formulation process, the EPO microspheres were subjected to an in vitro release test and antibody test in monkeys. As shown in FIG. 6, a nearly linear release of EPO was observed from the in vitro test. FIG. 7 compares the antibody responses of the EPO microspheres made according to the present disclosure and literature-report double emulsion method. Clearly, EPO microspheres prepared in the present disclosure had the similar antibody level as control groups of monkeys given NaCl solution and EPO solution dosage form.

What is claimed is:
1. A method to prepare polymeric microspheres of designed sizes and 90%+ encapsulation efficiency, comprising
   a) Pressing a solution of microsphere-forming materials to pass through a membrane possessing designed pore size into a receiving medium that is immiscible with the solution but dissolves the solvent of microsphere-forming materials in some extent;
   b) Applying a shear stress or a vibration to detach the embryonic microspheres formed by passing through the porous membrane in step a) from the membrane surface;
   c) Making the embryonic microspheres detached in step b) to move along a path filled with receiving medium parallelly without breaking by stirring and fusing by collision during sedimentation or flowing for extracting the solvent of the microsphere-forming materials into the receiving phase;
   d) Collecting the microspheres hardened by solvent extraction in step c).

2. The method of claim 1, wherein the porous membrane possesses defined pore size and is cylindrical, round, or planer in shape.

3. The method of claim 1, wherein the shear stress is generated by flowing or stirring the receiving medium which the porous membrane is placed in.

4. The method of claim 3, wherein the shear stress is generated by a nozzle which generates a straight flow through cylindrical porous membrane or a rounded flow around the porous membrane.

5. The method of claim 1, wherein the vibration is generated by shaking or beating the porous membrane or its holder outside or inside.

6. The method of claim 5, of which the frequency of generated vibration is adjusted between 100/min to 600/min.

7. The method of claim 6, of which the frequency of generated vibration is adjusted between 200/min to 400/min.

8. The method of claim 1, wherein the path of microsphere receiving medium is water-based, immiscible with the microsphere-forming solution, and able to extract the solvent of the microsphere-forming materials.

9. The method of claim 1, wherein the solution of the microsphere-forming materials is a polymer solution immiscible with water.

10. The method of claim 1, wherein the hardened microspheres are collected at the end of the path of microsphere-receiving medium.

11. The method of claim 1, wherein the path of microsphere-receiving medium is set as vertical, horizontal or in between.

12. The method of claim 1, wherein polymer solution is loaded with a bioactive agent.

13. The method of claim 12, wherein the bioactive agent is in particulate form suspending in the polymer solution by stirring or shaking.

14. The method of claim 1, wherein the collected hardened microspheres are transferred to a container for post microsphere-formation treatment and rinsing.

15. The method of claim 14, wherein a quality control unit is mounted within the path for transferring the microspheres to discriminate and eject oversized microspheres.

16. The method of claim 15, wherein the quality control unit consists a screen mesh to block the oversized microspheres and a three-way valve to eject the blocked microspheres out of the production line.

17. The method of claim 14, wherein post treatment comprises annealing the hardened microspheres for surface smoothing or for reducing solvent residues.

18. The method of 14, wherein the post-treatment container is equipped with floating socket to drain the liquids for post treatment or for rinsing from the top so as not to interrupt the sedimentation of the microspheres during the treatment.

19. The method of claim 1, wherein the bottom of the microsphere collector may shape as round, cylindrical, cone-shaped or in between of them.

20. The method of claim 1, wherein solvent to dissolve microsphere-forming polymers is methylene dichloride and the receiving phase is aqueous solution of polyvinyl alcohol and NaCl.

21. The method of claim 1, wherein a final formulation container is included to receive the post-treated microspheres, and to blend additives in.

* * * * *